(12) United States Patent  (10) Patent No.: US 9,198,642 B2
Storz  (45) Date of Patent: Dec. 1, 2015

(54) MEDICAL HANDHELD DEVICE AND POWER UNIT

(76) Inventor: Olaf Storz, Tuttlingen (DE)

( * ) Notice: Subject to any disclaimer, the term of this patent is extended or adjusted under 35 U.S.C. 154(b) by 196 days.

(21) Appl. No.: 13/615,952

(22) Filed: Sep. 14, 2012

(65) Prior Publication Data

US 2013/0072952 A1  Mar. 21, 2013

Related U.S. Application Data

(60) Provisional application No. 61/537,587, filed on Sep. 22, 2011.

(30) Foreign Application Priority Data

Sep. 14, 2011 (DE) .......................... 10 2011 113 127
Aug. 1, 2012 (DE) .......................... 10 2012 015 093

(51) Int. Cl.
| | |
|---|---|
| H02K 29/12 | (2006.01) |
| A61B 17/00 | (2006.01) |
| A61B 17/16 | (2006.01) |
| A61B 17/14 | (2006.01) |

(52) U.S. Cl.
CPC .................. *A61B 17/00* (2013.01); *A61B 17/16* (2013.01); *A61B 17/1622* (2013.01); *A61B 17/1626* (2013.01); *A61B 17/1628* (2013.01); *A61B 17/14* (2013.01); *A61B 17/148* (2013.01); *A61B 17/162* (2013.01); *A61B 17/1624* (2013.01); *A61B 2017/00477* (2013.01); *A61B 2017/00734* (2013.01)

(58) Field of Classification Search
CPC .... H01H 9/061; B25B 21/00; Y02T 10/7005; H02K 29/12

USPC ......... 318/139, 461, 400.37, 400.38; 388/937
See application file for complete search history.

(56) References Cited

U.S. PATENT DOCUMENTS

| | | | | |
|---|---|---|---|---|
| 3,734,207 | A * | 5/1973 | Fishbein ....................... | 173/217 |
| 4,233,737 | A * | 11/1980 | Poehlmann ..................... | 30/335 |
| 4,728,876 | A * | 3/1988 | Mongeon et al. .............. | 320/114 |
| 5,268,622 | A * | 12/1993 | Philipp ..................... | 318/400.08 |
| 5,382,249 | A * | 1/1995 | Fletcher ........................ | 606/79 |
| 5,553,675 | A * | 9/1996 | Pitzen et al. .................. | 173/217 |
| 5,581,165 | A * | 12/1996 | Laio .............................. | 318/261 |
| 6,059,806 | A * | 5/2000 | Hoegerle ....................... | 606/180 |
| 6,422,867 | B2 * | 7/2002 | Lang et al. .................... | 433/118 |
| 6,960,894 | B2 * | 11/2005 | Carusillo et al. ......... | 318/400.01 |
| 7,083,618 | B2 * | 8/2006 | Couture et al. ................. | 606/51 |
| 7,514,890 | B2 * | 4/2009 | Schneider et al. ............ | 318/432 |
| 8,067,916 | B2 * | 11/2011 | Auh et al. ..................... | 318/560 |
| 2003/0101526 | A1 * | 6/2003 | Hilscher et al. ................ | 15/22.1 |

(Continued)

*Primary Examiner* — Rina Duda
(74) *Attorney, Agent, or Firm* — Von Rohrscheidt Patents

(57) ABSTRACT

The present invention relates to a medical handheld device including at least one power unit, at least one power consumer, at least one actuation element and at least one switching device which is movable from a first switching position into a second switching position when the actuation element is actuated. The invention also relates to a power unit for use in a handheld device according to the invention. The invention also relates to a power unit for use in a medical handheld device, wherein the power unit includes at least one power consumer, at least one power source, and at least one switching device which is arranged to be moved from a first switching position into the second switching position when the actuation element is actuated by the user to provided power from the voltage source to operate the power consumer and/or the handheld device.

11 Claims, 7 Drawing Sheets

(56) References Cited

U.S. PATENT DOCUMENTS

2006/0206100 A1* 9/2006 Eskridge et al. .................. 606/1
2006/0217729 A1* 9/2006 Eskridge et al. ................ 606/80
2009/0216229 A1* 8/2009 Chojin ........................... 606/52
2012/0303002 A1* 11/2012 Chowaniec et al. ............. 606/1

* cited by examiner

MEDICAL HANDHELD DEVICE AND POWER UNIT

RELATED APPLICATIONS

This application claims priority from and incorporates by reference German Patent Application DE 10 2011 113 126.8, filed on Sep. 14, 2011, German Patent Application De 10 2012 015 091.1, filed on Aug. 8, 2012 and U.S. Provisional Patent Application 61/537,587 filed on Sep. 22, 2011.

FIELD OF THE INVENTION

The present invention relates to a medical handheld device. It furthermore relates to power units according for the handheld medical device.

BACKGROUND OF THE INVENTION

Medical handheld devices like handheld drills or handheld saws and similar are known in the art which are usable with rechargeable voltage sources and thus transportable. Handheld devices of this type can be used independently from an access to a power grid until the voltage source used has reached a respectively low charging condition.

BRIEF SUMMARY OF THE INVENTION

Thus, it is an object of the present invention to provide another handheld device of this general type with a power unit or a power pack which includes the voltage source for the handheld device. Furthermore, a suitable power unit shall be provided.

The object of the invention is achieved through a handheld medical device including at least one power unit which includes at least one voltage source; at least one power consumer; at least one actuation element for actuation by a user for providing power from the voltage source for operating the handheld device; and at least one switching device which is movable between at least a first switching position in which a conductive connection between the power consumer and the voltage source is being interrupted or is interrupted through the switching device and at least a second switching in position in which the conductive connection between the power consumer and the voltage source is not being interrupted or not interrupted by the switching device, wherein the switching device is movable from the first switching position into the second switching position when the actuation element is being actuated. It is furthermore achieved through a power unit for use in a medical handheld device which is in particular configured according to one of the preceding claims, the power unit including at least one power consumer; at least one power source; at least one switching device which is movable between at least a first switching position in which a conductive connection between the power consumer and the voltage source is being interrupted or is interrupted through the switching device and at least a second switching position in which the conductive connection between the power consumer and the voltage source is not interrupted or being interrupted by the switching device, wherein the switching device is arranged to be moved by a user of the handheld device from the first switching position into the second switching position when the actuation element is actuated in order to provide power from the voltage source to operate a power consumer and/or the handheld medical device.

For this purpose, the present invention proposes a medical handheld device (also abbreviated handheld device) with a power unit (synonym: power pack) which includes at least one voltage source and at least one power consumer. Furthermore, the medical handheld device includes at least one actuation element through which the user of the handheld device through respective actuation can draw power from the voltage source for operating the power consumer and/or the handheld device thus for sawing, drilling, etc. Furthermore, the handheld device includes at least one switching device. The switching device is movable or switchable between at least one first switching position in which a conductive connection (this is also a power connection or a voltage connection) is being interrupted or is interrupted through the switching device between the power consumer and the power source and at least a second switching position in which the conductive connection between the power consumer and the voltage source is not being interrupted or is interrupted through the switching device. Thus, the switching device is arranged to be moved from a first switching position into a second switching position when the actuation element is actuated.

The present invention furthermore includes a power unit which is arranged provided or configured to be used in the handheld device according to the invention.

Furthermore, the present invention includes a power unit for use in a medical handheld device, in particular a medical handheld device according to the invention. Thus, the power unit includes at least one power consumer and at least one voltage source. Furthermore, the power unit includes at least one switching device which is movable between at least a first switching position in which a conductive connection is interrupted between the power consumer and the voltage source through the switching device and at least a second switching position in which the conductive connection between the power consumer and the voltage source is not interrupted through the switching device. Thus, the switching device is arranged to be moved from the first switching position into the second switching position during or through or as a function of the actuation of an actuation element by the user of the handheld device for drawing a power from the voltage source for operating the power consumer and/or the handheld device.

Advantageous embodiments of the present invention are respectively objects of the dependent claims and embodiments recited therein.

Embodiments according to the invention can include one or plural features recited infra.

In all subsequent statements, the term "can be" or "can have", etc., is synonymous with "is advantageously" or "has advantageously", etc., and intended to describe an embodiment according to the invention.

Embodiments according to the invention can have one, all, or plural of the advantages recited supra or infra.

In some embodiments according to the invention, interrupting the conductive connection is a physical interruption of the conductive connection between a power consumer and a voltage source. An interruption can be a bodily or physical disconnection or prevention of the conductive connection (for example power conductor, voltage cable, strand, etc.).

In a disconnected and/or interrupted condition in some embodiments according to the invention, no minimum current runs between the power consumer and the power source, not even in the sense of a so-called sleep function or standby function.

In a separated and/or interrupted condition, no current embodied as a leak current flows in particular embodiments according to the invention.

In some embodiments according to the invention, interrupting the conductive connection is a galvanic separation between a power consumer and a power source.

In particular embodiments according to the invention, interrupting the conductive connection prevents a voltage and/or energy exchange between the power unit on the one hand side and a motor, circuit board for motor control and/or the handheld device on the other hand side.

In some embodiments according to the invention, the at least one voltage source of the power unit according to the invention is a rechargeable voltage source.

In other embodiments according to the invention the voltage source is a replaceable voltage source, preferably it is removable from the power unit during normal operations.

In particular embodiments according to the invention, the voltage source is an accumulator or a battery, a combination thereof or respectively includes a plurality thereof (thus two, four, six or more accumulator cells). The actuation element, in some embodiments according to the invention is a hand switch, a foot switch, a key switch, turning knob, toggle switch or similar. The actuation element can furthermore be or include a combination of the actuation elements recited supra and/or additional actuation elements.

In some embodiments according to the invention, the actuation element includes an actuation path. The actuation path in some embodiments according to the invention is configured as a movement path or similar.

In some embodiments according to the invention, the actuation element is actuatable in more than two different positions, for example it can be moved back and forth. In some embodiments according to the invention, this is the case along its actuation path. Thus a different activity of the power consumer is provided in each of these positions, for example in the form of different speeds, or it results therefrom.

The actuation element in some embodiments according to the invention is preferably entirely or at least through a portion of its movement path actuatable in a continuously variable manner. Thus, in some embodiments according to the invention a different, e.g. continuously increasing or decreasing activity of the power consumer is provided.

In some embodiments according to the invention, the actuation element is preferably actuated against a spring or a spring device. Respective devices are provided in these embodiments.

In particular embodiments according to the invention, the actuation element is neither a toggle switch nor an on-off switch.

In particular embodiments according to the invention, the power consumer is at least one motor, at least one motor circuit board, or both.

In some embodiments according to the invention, a conductive connection is completely interrupted through the switching device in its first switching position.

The switching device in particular embodiments according to the invention is completely in an interior of the handheld device and/or it is not directly operable by the user when the handheld device is being used.

In some embodiments, the handheld device according to the invention furthermore includes at least one device which is configured to move the switching device into the first switching position and/or to keep the switching device in the first switching position when or as long as the actuation element is not actuated.

This device in particular embodiments according to the invention is a spring or a reset spring.

The handheld device according to the invention in some embodiments furthermore includes at least one element that is movable between at least two positions, a first position and a second position, wherein the element is arranged and/or linked or mechanically or otherwise connected so that its first or second position assumed by it for example at a particular point in time for example relative to a non-movable section of the handheld device or the power unit corresponds to a degree or measure of actuation of the actuation element or represents the degree or measure of actuation.

Furthermore, the handheld device according to the invention in these embodiments includes at least one processing device configured for processing or detecting at least one of the positions of the movable element. In these embodiments, the handheld device according to the invention furthermore includes at least one control or regulation device which is arranged, provided and/or configured for putting out power- or voltage or for limiting or releasing the put-out power or voltage of the voltage source to the power consumer as a function of the processed or detected position of the movable element and/or in view of this position.

In some embodiments according to the invention, the control- or regulation device is part of a potentiometer, in particular of a linear potentiometer or it includes a potentiometer or is embodied as a potentiometer.

In some embodiments of the handheld device according to the invention, the element that is movable between at least two positions is arranged to be moved from the first position into a second position through the actuation of the actuation element and/or to be moved from the second position into the first position.

In particular embodiments of the handheld device according to the invention, the element that is movable between at least two positions is arranged to move the switching device from the first switching position to the second switching position through the movement of the element.

In some embodiments of the handheld device according to the invention, the processing device is configured to detect and process the position assumed by the movable element in a mechanical, inductive, resistive, optical and/or capacitive manner.

In some embodiments of the handheld device according to the invention, the element that is movable between at least two positions and/or the processing device and/or the control or regulation device is part of a linear potentiometer.

In particular embodiments of the handheld device according to the invention the element that is movable between at least two positions and/or the processing device and/or the control or regulation device is arranged to move the switching device from the first switching position into the second switching position which provides a conductive connection or voltage supply that has not existed before and which is required for "reading out" or effectivity of the potentiometer, for example the linear potentiometer.

In some embodiments of the handheld device according to the invention, no voltage is applied, for example at the linear potentiometer, at the voltage input and/or at all voltage outputs of the potentiometer in the first switching position.

In some embodiments of the handheld device according to the invention, the power unit includes the power consumer, the power source and the switching device.

In particular embodiments of the handheld device according to the invention, the power unit includes the arrangement which is configured to bring the switching device into the first switching position or to keep the switching device in the first switching position when or as long as the actuation element is not actuated and/or the element that is movable between at least two positions and/or the processing device which is configured for processing and/or detecting at least one of the positions of the movable element and/or the at least one control or regulation device for limiting and/or releasing the put-out power as a function of the processed or detected position of the movable element.

In some embodiments of the handheld device according to the invention, the power unit is removably arranged in the handheld device or provided for this purpose.

In particular embodiments according to the invention, the handheld device is configured as a drill, a saw, an oscillating saw, a sagittal saw, cutting wire chuck, as a laser device or as a combination thereof.

In particular embodiments according to the invention, the control- or regulation device does not release power when or as long as the switching device is in the first switching position in which a voltage transmission is interrupted.

In some embodiments according to the invention, the switching device does not release any power when or as long as it is in the first switching position in which a voltage transmission is interrupted.

In some embodiments according to the invention, the switching device operates according to a mechanical, inductive, resistive, optical, capacitive, etc. principle or is switched based on such principle.

In some embodiments according to the invention, a position of the at least one element that is movable, adjustable or switchable between at least two positions, wherein the element reflects a degree of actuation of the actuation element and is determined, identified or processed according to a mechanical, inductive, resistive, optical, capacitive, etc. principle or based thereon.

The power unit according to the invention in some embodiments furthermore includes at least one arrangement which is configured to move the switching device into the first switching position or to keep the switching device in the first switching position when or as long as the actuation element is not actuated. In these embodiments, the power unit in a supplementary or alternative manner includes at least the element that is movable between at least two positions or at least one processing arrangement that is configured for processing or detecting at least one of the positions of the movable element and/or the at least one control or regulation device for limiting and/or releasing the put-out power as a function of the processed or detected position of the movable element or based thereon.

In particular embodiments according to the invention, the handheld device includes at least one housing section which is made from aluminum, titanium, stainless steel, plastic material, carbon material, composite material, a fiber reinforced plastic material or a combination hereof, or which includes one of the materials recited supra. In some embodiments according to the invention, the housing of the handheld device is made from the same material as the housing section.

One or plural of the advantages recited supra or infra can be achieved with the embodiments according to the invention.

One advantage of the present invention is the ability to totally switch off the handheld device in moments in which no power is required from the handheld device. This reduces or prevents in an advantageous manner to lose power through leaking currents or similar. This is particularly advantageous when the power unit is stored for longer time periods. Therefore, this advantage can always be achieved when the power unit is arranged in the handheld device but the handheld device is not being used.

A total switch-off in particular embodiments according to the invention is a separation of at least one motor or all motors and/or one or all motor circuit boards.

It is another advantage that the optional total switch-off can be performed in a purely mechanical manner. The latter represents a robust configuration that has very little damage propensity.

It is furthermore advantageous that the total switch-off is performed self-acting as soon as or as long as the actuation element, for example a hand push button is not activated. Thus the user does not have to become active and the hand push button furthermore cannot be forgotten.

It is another advantage that for saving electrical energy in the motor circuit board or at another location, no sleep function or power down function has to be provided according to the invention and/or that its effect is taken over by a configuration according to the instant invention.

It can furthermore be advantageous that only a very small power draw is caused when the switching device through which the power cut-off is caused is removed again, this means when the switching device is moved between the switching positions. This way the service life of the switch can be advantageously extended.

BRIEF DESCRIPTION OF THE DRAWINGS

The present invention is subsequently described with reference to partially highly simplified drawing figures in which identical reference numerals designate identical or like components, wherein.

DETAILED DESCRIPTION OF THE INVENTION

Figure 1:
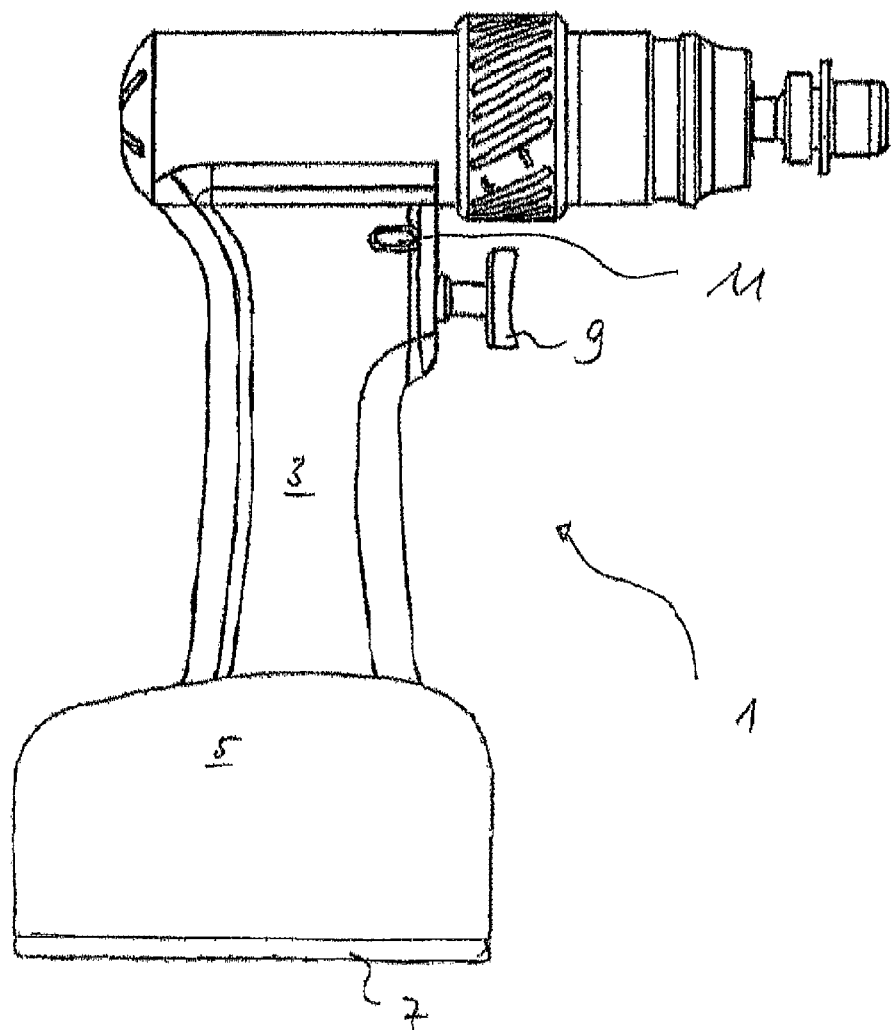
FIG. 1 illustrates a medical handheld device according to the invention in an exemplary embodiment in a lateral view.

FIG. 1 illustrates a handheld device 1 according to the invention. The handheld device is configured in the present embodiment in an exemplary manner as a surgical drill.

The handheld device 1 includes a handle 3 which transitions into a receiving section 5 for a power unit that is not evident in FIG. 1.

The receiving section 5 is closed through a handheld device cover 7 which can be opened for inserting or removing the power unit into or from the handheld device 1.

The handheld device cover 7 in some embodiments according to the invention is connected or provided preferably through one or plural hinges that are not illustrated at the receiving section 5 or another section of the handheld device 1.

The handheld device 1 includes an actuation element 9 for actuation by a user. The actuation element 9 is configured as a hand switch in an exemplary manner. The hand switch can be actuated through pressing. When the hand switch is being pressed, a power consumer, thus the motor for drilling operation of the handheld device 1 begins to operate or put differently to consume power. The activity of the motor, e.g. its speed, can be predetermined through the amount of pressing the hand switch or through the depth to which the actuation element 9 is pressed. The actuation element 9 in the illustrated embodiment is continuously actuatable or over plural positions entirely or at least over a portion of its movement path. Depending on how strong or deeply the actuation is pressed, an individual, differently configured actuation of the motor, for example an individual speed is caused. An actuation can be performed for example against a spring or a spring device.

A right running/left running switch 11 is provided to be able to predetermine the rotational direction of the drill chuck of the handheld device 1.

Figure 2:
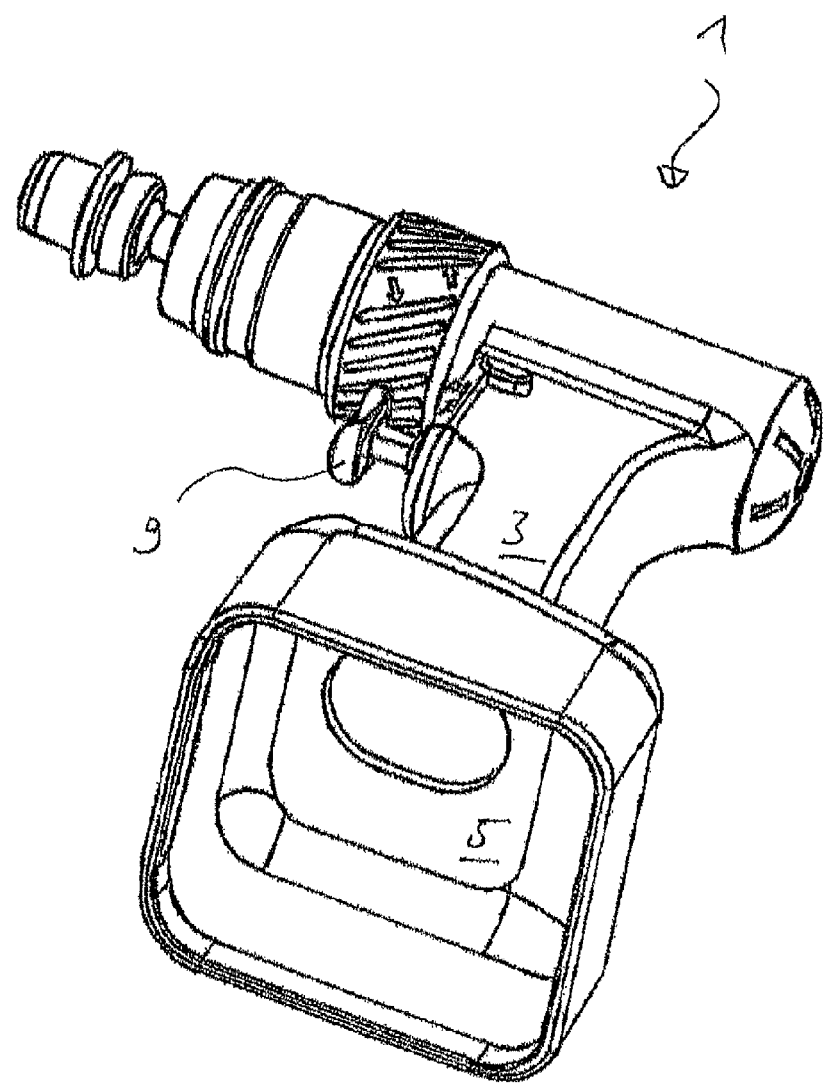
FIG. 2 illustrates the handheld device according to the invention in a perspective view at a slant angle from below.

FIG. 2 illustrates the handheld device 1 according to the invention in a perspective view at a slant angle from below. The handheld device cover 7 is removed. The power unit is removed from the handheld device 1 and therefore in turn not illustrated.

Figure 3:
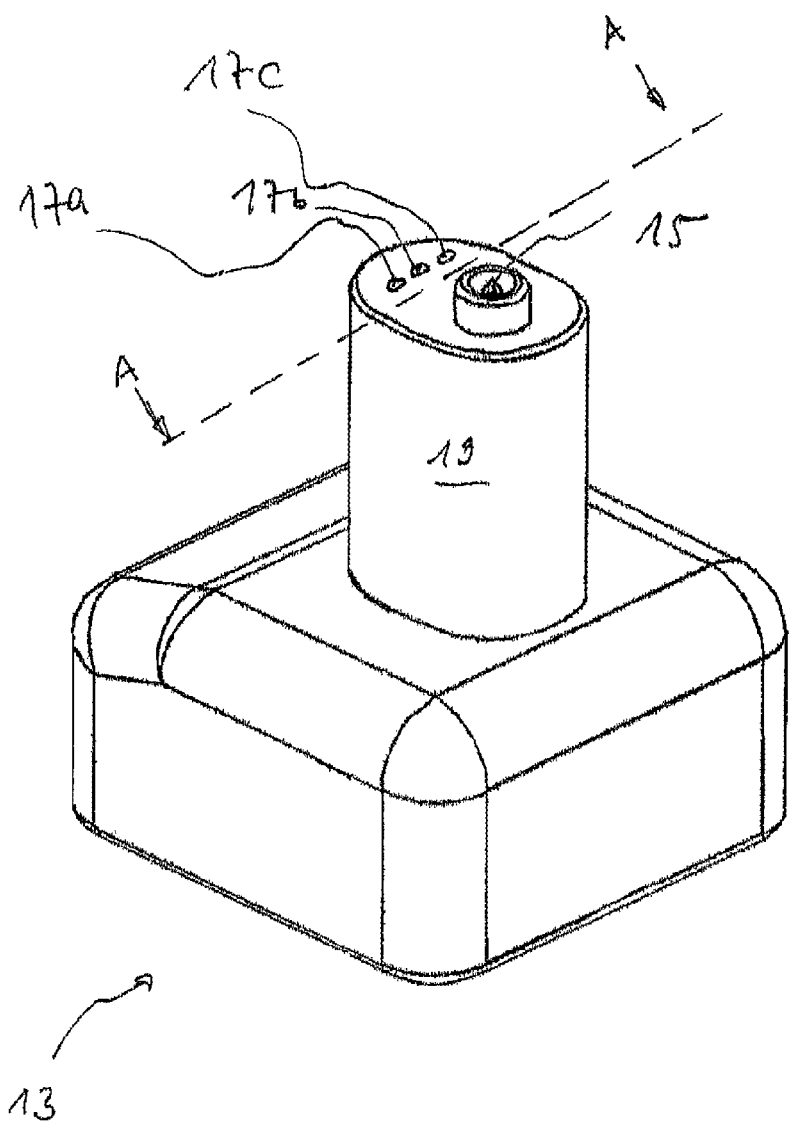
FIG. 3 illustrates the power unit according to the invention of the handheld device according to the invention in an exemplary embodiment in a perspective view at a slant angle from above.

FIG. 3 illustrates an exemplary power unit 13 according to the invention for use with the handheld device 1 according to the invention (thus according to FIG. 1 or 2) in a perspective view at a slant angle from above.

The power unit 13 also designated as power pack includes the voltage source for the handheld device 1 and a motor as a power consumer. It furthermore includes one or plural control- or regulation devices which are required for operating the handheld device 1 or its components in case their operation requires an electrical voltage.

In the embodiment illustrated in FIG. 3, the power unit 13 includes the entirety of all electrical and/or electronic components, thus power consumers and/or power conducting components of the handheld device 1 that is ready to use. As apparent from FIG. 3, the power unit 13 includes a coupling that is connected with the motor that is not illustrated or an end of an output shaft 15. The power unit 13 furthermore includes control connections 17a, 17b, and 17c. Through the control connections 17a, 17b, 17c signals can be transmitted by the user of the handheld device 1 to the power unit 13 for example through the actuation element 9 or through the right-/left-running switch 11. The power unit 13 in turn controls or regulates the motor and thus the speed and the torque, the rotation direction or similar of the output shaft based on the signals thus received.

The output shaft 15 and also the control connections 17a, b, c are accessible from a face side of a housing section 19 of the power unit 13, wherein the motor is arranged behind the face side. This arrangement is purely exemplary. Other embodiments than the embodiment illustrated in FIG. 3 are also included by the present invention.

Figure 4:
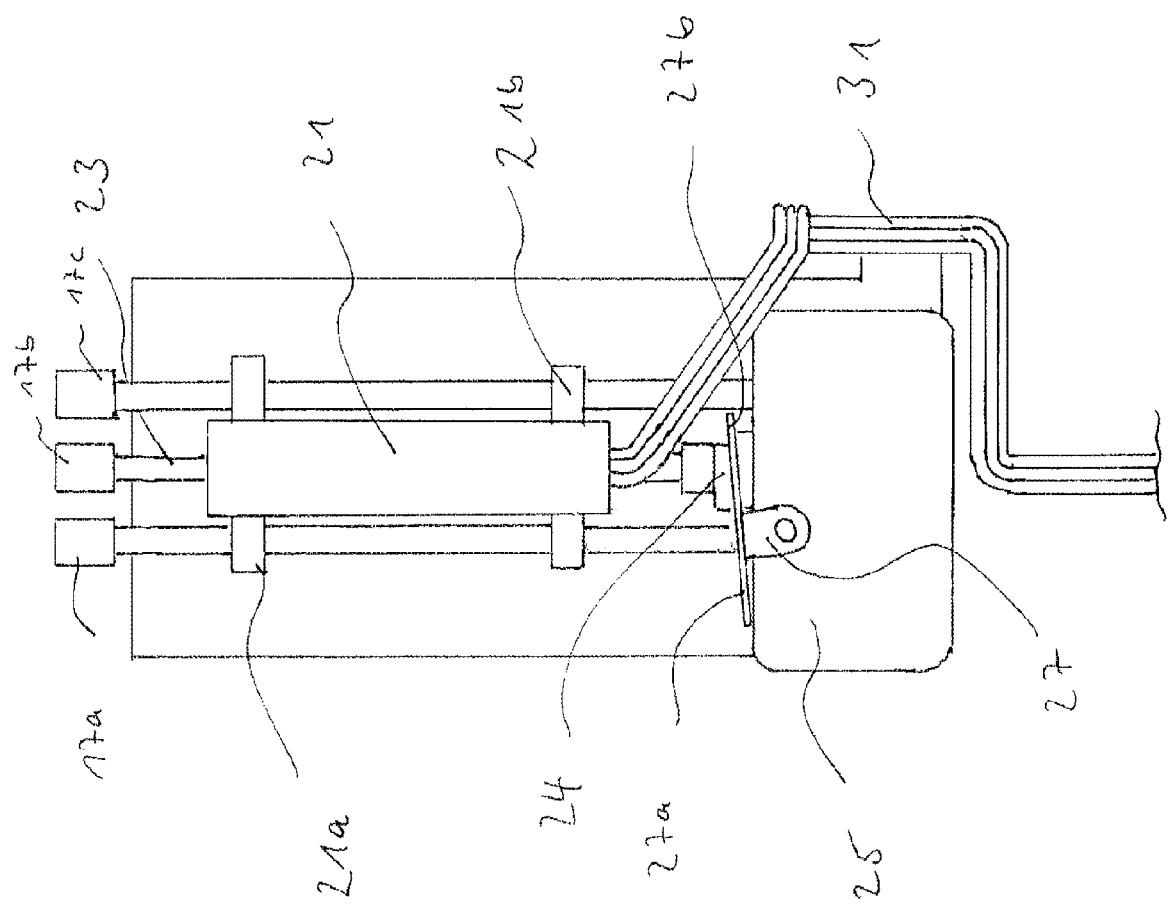
FIG. 4 illustrates a detail of a sectional view along the dashed line A-A of FIG. 3 of the power unit according to the invention.
Figure 5:
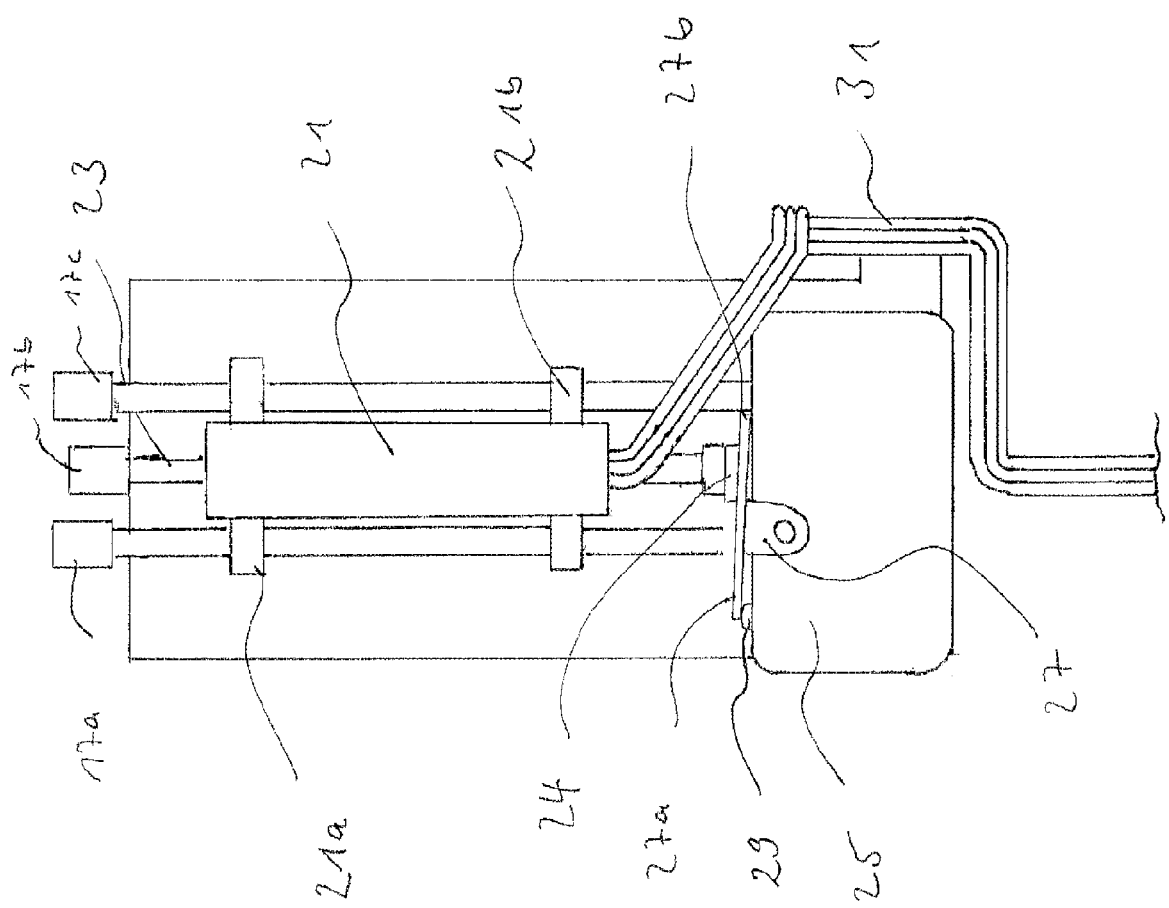
FIG. 5 illustrates a sectional view of the power unit according to the invention of FIG. 4.
Figure 6:
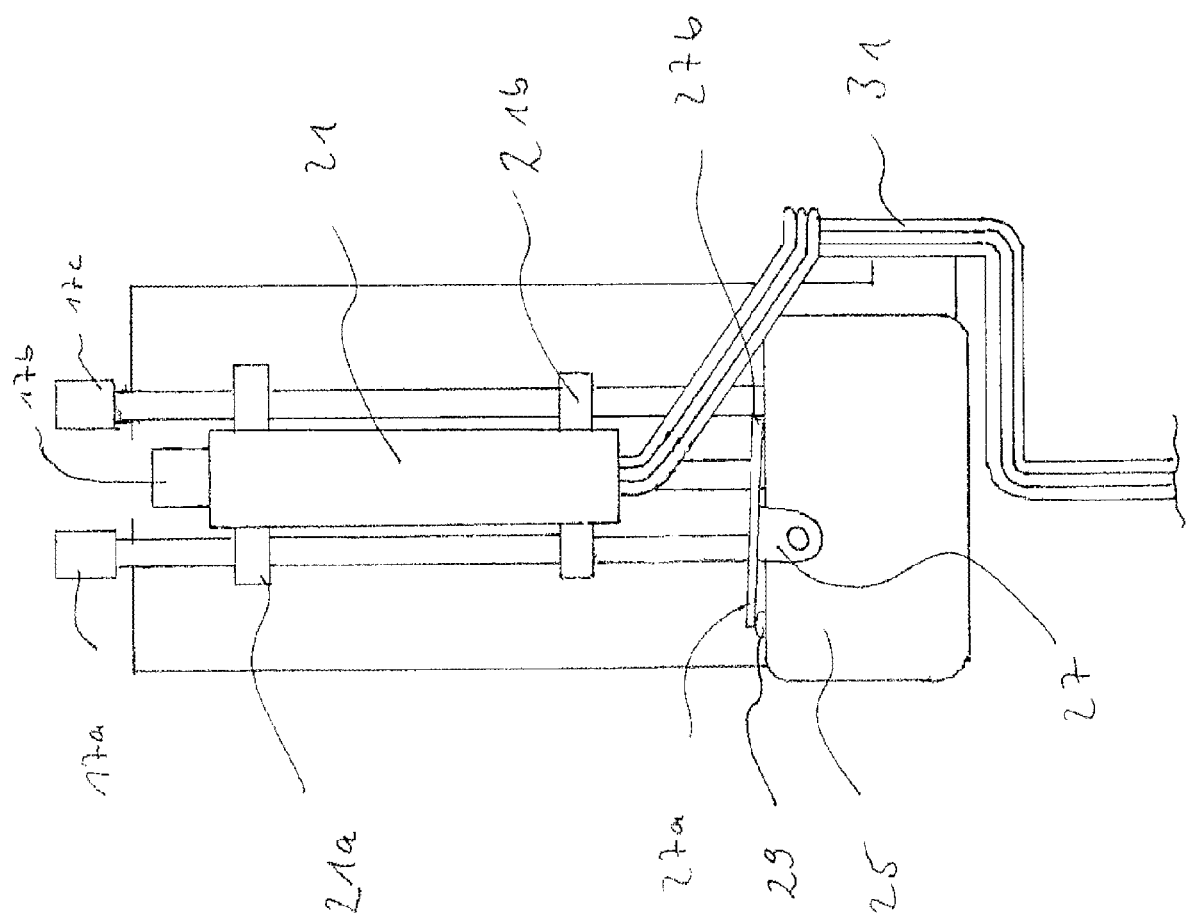
FIG. 6 illustrates a sectional view of the power unit according to the invention according to FIGS. 4 and 5.

FIGS. 4 through 6 illustrate a detail of the power unit 13 according to the invention. Thus, a sectional plane is illustrated in which the dashed line A-A of FIG. 3 is disposed. Only details of the sectional plane are illustrated.

The items illustrated in FIGS. 4 through 6 are arranged within the housing section 19 with reference to the illustration of FIG. 3. FIGS. 4 through 6 illustrate the control connections 17a, 17b, 17c known from FIG. 3. These can be actuated or pressed through plungers that are not illustrated, for example in a purely mechanical manner. The plungers can in turn be actuated through the actuation element 9 or the right/left rotation switch 11 through applying pressure in a top down direction with reference to the illustration of FIGS. 4 through 6. This is performed optionally against a spring force of springs that are not illustrated.

FIGS. 4 through 6 illustrate a linear potentiometer 21 which is attached in the power unit 13 through pins 21a and 21b. The linear potentiometer 21 includes a potentiometer plunger 23 supported in the linear potentiometer wherein the potentiometer plunger 23 includes an insert 24. The potentiometer plunger 23 is arranged in the linear potentiometer 21 so that it is movable downward through pressure on the control connection 17b against the spring force of a spring that is not illustrated.

A switching device 25 is apparent in FIGS. 4 through 6 from the extension of the linear potentiometer 21 in downward direction wherein the switching device includes a switch toggle 27 with two pivot legs 27a and 27b. The switching device 25 is used for complete power interruption and/or voltage interruption between a voltage source that is not illustrated, the power unit 13 and the power consumer, thus the motor of the handheld device 1 or a motor circuit board. A complete power or voltage interruption through interruption of conduction is provided when the switch toggle 27 is inclined like in FIG. 4 which illustrates a first switching position of the switching device 25. The switching position illustrated in FIG. 4 is taken by the switching device 25 when the actuation element 9 is not actuated or pressed. In this first switching position, a transmission of power, current and/or voltage from the power source, e.g. an accumulator or a battery is prevented by interrupting the voltage carrying conductor. An unintentional discharge is thus excluded as long as this unintentional discharge is due to subsequent electrical components or consumers like circuit boards, motors, etc.

The switch toggle 27 is kept in the position or inclination illustrated in FIG. 4 through a non-illustrated spring. In this position, the switch toggle supports an interrupter button 29 in an interrupting condition with its first toggle leg 27a disposed on the left side in FIG. 4, wherein the interrupter button 29 is disposed in an interior of the switching device 25 and therefore not visible in FIG. 4, wherein the interrupting position is also designated as an open switching position.

The handheld device 1 or the electrics of the power unit 13 are arranged so that a read-out and/or processing of the position of the potentiometer plunger 23 which is arranged in a first position in FIG. 4 is not provided in the open or first switching position of FIG. 4. This is determined by the fact that no voltage is applied to the linear potentiometer 21 as an embodiment of the device for reading out the switching position of the switching device 25 illustrated in FIG. 4 due to the instant switching position. Also this helps with saving energy and advantageously counteracts a discharge.

The other components which are illustrated in FIGS. 4 through 6 are among others an electrical conductor 31 for the linear potentiometer 21.

FIG. 5 illustrates a condition of the switching device 25 which can only be reached when the actuation element 9 is depressed. In FIG. 5, the switching device 25 due to the inclination of the switch toggle 27 that is changed over FIG. 4 is in a second closed switching position. The changed inclination of the switch toggle 27 is provided since the potentiometer plunger 23 was moved downward with reference to the illustration in FIG. 5. Thus, the potentiometer plunger 23 transitions from the first position into the second position. When moving the potentiometer plunger 23 from the first position into the second position, the potentiometer plunger presses indirectly or directly for example with its insert 24 onto a protrusion 27c of a second toggle leg 27b of the rotatably or pivotably supported switch toggle 27, wherein the toggle leg 27b is arranged in the right of FIG. 5 and wherein the protrusion 27c protrudes freely in backward direction beyond the switching device 25 and however is not visible in FIG. 5. Thus the switch toggle 27 starts to incline, pivot or rotate accordingly clockwise with reference to the drawing plane about its pivot or rotating connection with the switching device 25.

The potentiometer plunger 23 is transferred through pressure onto the center control connection 17 from its first position into its second position. The device used for imparting pressure onto the control connection 17 (another plunger or pin supported by the plunger support) which is associated with the handheld device 1 but not with the power unit 13 and which is mechanically coupled with the actuation element 9 is not illustrated in any of the figures.

The changed inclination of the switch toggle 27, relative to the inclination of FIG. 4 causes or facilitates that differently from FIG. 4, FIG. 5 and FIG. 6, the interrupter button that is evident now is run out of the switching device 25 through the left toggle leg. In this second closed switching position of the switching device 25 and of the interrupter button 29, a transmission of power, current and/or voltage from the power source to subsequent or supplied electrical components or power consumers is not interrupted. The transfer is rather provided in this position. At least a transfer can be provided in as far as the switching device 25 is concerned.

In this closed or second switching position, differently from the first or open switching position of FIG. 4, a readout and/or processing of the position of the potentiometer plunger 23 is provided. A power supply required for this purpose is now provided. According to the processing of the position of the potentiometer plunger 23 or based thereon or relative thereto, the supplied electrical components or power consumers like circuit boards motors etc. are provided with current or power. Due to the actual inclination or actuation of the pivot toggle 27 as illustrated in FIG. 5, the motor will run with a first rather slow speed.

It is apparent that the potentiometer plunger 23 can assume more than only a second position in which the switching device 25 in turn is in the closed or second switching position and a power connection between the power source and the power consumer is provided. Depending on the degree or distance of its movement within the power unit 13 and in particular within the linear potentiometer 21, the potentiometer plunger 23, due to a more or less pronounced movement of the associated control connection 17b, can take any number of positions within the power unit 13. In each of these positions a voltage can be applied that is a function of the position, a speed can be provided or as a function of the provided regulation. The closed second switching position can therefore also be interpreted in some embodiments according to the invention as a plurality of sub switching positions or intermediary switching positions. They have in common that a readout and/or processing of the position of the potentiometer plunger 23 is provided and a voltage is applied or power can be tapped through the power consumer. They differ preferably only through the size of the supplied voltage, the reached speed, the size of the tapped power or similar.

FIG. 6 in turn illustrates a second closed switching position in which the linear potentiometer 21 is provided with power. Therefore, a readout and/or processing of the position of the potentiometer plunger 23 is also provided in the arrangement of FIG. 6 as already provided in the second closed switching position that is illustrated in FIG. 5, but differently from the first or open switching position that is illustrated in FIG. 4. The supplied electrical components or power consumers receive voltage, current or power according to the processing of the position of the potentiometer plunger 23 or based thereon or relative thereto.

The control connection 17b is in FIG. 6 evidently lower than in FIG. 5. Put differently, it is in a lower position compared to FIG. 5. This lower position comes as a consequence since the actuation element was pressed more firmly than in FIG. 5. In some embodiments according to the invention, the position depends from the degree or measure of the actuation of the actuation element 9 or is caused by it, preferably in a linear manner or relative thereto. Due to the position of the potentiometer plunger 23 that is determined to be lower by the linear potentiometer 21, the motor will run in FIG. 6 with a second, rather higher speed which is higher than the speed with which the motor runs for a position of the potentiometer plunger 23 that is illustrated in FIG. 5.

Figure 7:
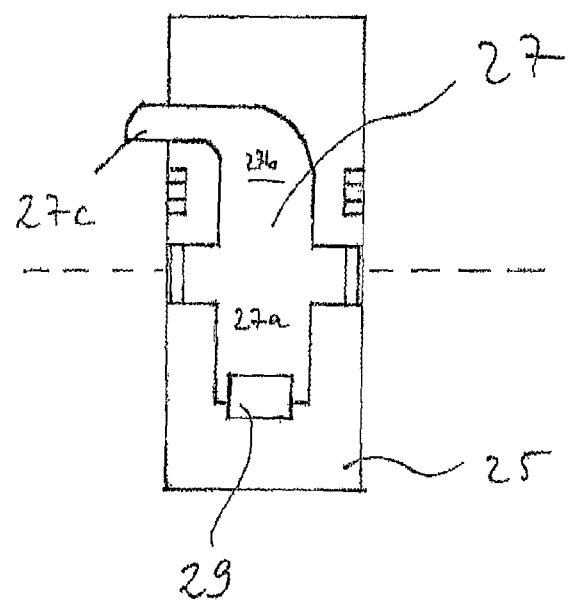
FIG. 7 illustrates a switching device of the power unit according to the invention according to FIG. 4 through 6 in a perspective from above.

FIG. 7 illustrates the switching device 25 with the switch toggle 27 resting thereon and rotatably connected therewith in a view from above. The electrical input- and output conductors are not illustrated in FIG. 7 for better visibility. The protrusion 27c is visible which can be depressed through the potentiometer plunger 23 or its insert 24, this means into the drawing plane of FIG. 7. When pressure is applied onto the protrusion 27c, the switch toggle 27 can be rotated by a limited amount about the rotation axis indicated by the dashed line. Thus, the first toggle leg 27 by being lifted facilitates that the interrupter button 29 can transition from the first switching position into the second switching position, wherein the first toggle leg 27a contacts the interrupter button 29, wherein the interrupter button 29 is kept depressed, for example against the effect of a spring. An alternative configuration according to the invention provides that the interrupter button 29 is force guided for example by the toggle leg 27a.

REFERENCE NUMERALS AND DESIGNATIONS 1 handheld device
3 handle
5 receiving section
7 handheld device cover for receiving section
9 actuation element for user actuation
11 right-/left-running switch
13 power unit
15 drive shaft
17a, b, c control connections
19 housing section
21 linear potentiometer
21a, b pins
23 potentiometer plunger
24 insert for potentiometer plunger
25 switching device
27 switch toggle
27a first toggle leg
27b second toggle leg
27c protrusion of the second toggle leg 27b
29 interrupter button
31 electrical conductor for linear potentiometer 21

What is claimed is:
1. A handheld medical device, comprising:
at least one power unit which is removably arranged in the handheld medical device and includes the entirety of all power consumers or power conducting components of the handheld medical device, at least a voltage source, at least a switching device; and
at least one actuation element for actuation by a user for providing power from the voltage source for operating the handheld device; and at least one device that moves the switching device into the first switching position when or as long as the actuation element is not being actuated, wherein the switching device is movable between at least a first switching position in which a conductive connection between the power consumer and the voltage source is being interrupted so that a voltage or energy exchange between the power unit and the power consumer is prevented or is interrupted through the switching device and at least a second switching in position in which the conductive connection between the power consumer and the voltage source is not being interrupted or not interrupted by the switching device, wherein the switching device comprises at least one element that is movable between two positions and a switch toggle that is rotatable between two positions, wherein the switching device is movable from the first switching position by the movable element and the rotatable switch toggle into the second switching position when the actuation element is being actuated, wherein the movable element is configured so that a position taken by the movable element corresponds to a degree of actuation of the actuation element or reflects the degree of actuation of the actuation element, and wherein the element that is movable between the at least two positions is a portion of a linear potentiometer.

2. The handheld device according to claim 1, further comprising:

at least one processing device for processing or detecting at least one of the positions of the movable element; and at least one control- or regulation device for limiting or releasing the power of the voltage source to the voltage consumer as a function of a processed or detected position of the movable element.

3. The handheld device according to claim 2, wherein the at least one element that is movable between at least two positions is movable upon actuation of the actuation element from the first position into the second position or from the second position into the first position.

4. The handheld device according to claim 2, wherein the element that is movable between at least two positions moves the switching device from the first switching position into the second switching position during or through its movement.

5. The handheld device according to claim 2, wherein the processing device detects or processes the position of the movable element in a mechanical, inductive, resistive, optical or capacitive manner.

6. The handheld device according to claim 1, wherein the power unit further includes the following:

an arrangement which brings the switching device into the first switching position when or as long as the actuation element is not actuated; or the movable element that is movable between at least two positions; or a processing device configured for processing or detecting at least one of the positions of the movable element; or at least one control- or regulation device for limiting or releasing the power as a function of the processed or detected position of the movable element.

7. The handheld device according to claim 1, wherein the handheld device is a drill, an oscillating saw, a sagittal saw or as a combination thereof.

8. The handheld device according to claim 1, wherein the power unit includes the following:

the arrangement which brings the switching device into the first switching position when or as long as the actuation element is not actuated;

the element that is movable between at least two positions;

the processing device for processing or detecting at least one of the positions of the movable element; and the at least one control- or regulation device for limiting or releasing the power as a function of the processed or detected position of the movable element.

9. A power unit for use in a medical handheld device, the power unit comprising:

at least one motor or at least one motor circuit board;

at least one power source;

at least one switching device which is movable between at least a first switching position in which a conductive connection between the power consumer and the voltage source is being interrupted or is interrupted so that a voltage or energy exchange between the power unit and the power consumer is prevented through the switching device and at least a second switching position in which the conductive connection between the power consumer and the voltage source is not interrupted or being interrupted by the switching device, wherein the switching device comprises at least one element that is movable between two positions and a switch toggle that is rotatable between two positions, wherein the switching device is movable by a user of the handheld device from the first switching position into the second switching position when the actuation element is actuated and by the movable element and the rotatable switch toggle in order to provide power from the voltage source to operate a power consumer or a handheld medical device, wherein the movable element is configured so that a position taken by the movable element corresponds to a degree of actuation of the actuation element or reflects the degree of actuation of the actuation element, wherein the power unit further comprises at least one device that moves the switching device into the first switching position when or as long as the actuation element is not being actuated, and wherein the element that is movable between the at least two positions is a portion of a linear potentiometer.

10. The power unit according to claim 9, further comprising:

the at least one element that is movable between two positions; or at least one processing device for processing or detecting at least one of the positions of the movable element; or at least one control- or regulation device for limiting or releasing the output power as a function of the processed or detected position of the movable element.

11. The power unit according to claim 9, further comprising:

the at least one arrangement that moves the switching device into the first switching position when or as long as the actuation element is not actuated;

the at least one processing device for process ng or detecting at least one of the positions of the movable element; and at least one control- or regulation device for limiting or releasing the power as a function of the processed or detected position of the movable element.

* * * * *